(12) United States Patent
Weibel (10) Patent No.: US 9,080,681 B2
(45) Date of Patent: Jul. 14, 2015

(54) DEVICE FOR WITHDRAWING LIQUID FROM A CONTAINER

(75) Inventor: Ludwig Daniel Weibel, Waldstatt (CH)

(73) Assignee: WEIBEL CDS AG, Waldstatt (CH)

( * ) Notice: Subject to any disclaimer, the term of this patent is extended or adjusted under 35 U.S.C. 154(b) by 93 days.

(21) Appl. No.: 13/992,373

(22) PCT Filed: Dec. 14, 2011

(86) PCT No.: PCT/EP2011/072716
§ 371 (c)(1),
(2), (4) Date: Jul. 29, 2013

(87) PCT Pub. No.: WO2012/080310
PCT Pub. Date: Jun. 21, 2012

(65) Prior Publication Data
US 2013/0306169 A1 Nov. 21, 2013

(30) Foreign Application Priority Data
Dec. 17, 2010 (EP) .................................. 10195706

(51) Int. Cl.
*F16K 24/00* (2006.01)
*F16L 29/00* (2006.01)
*A61M 5/162* (2006.01)

(52) U.S. Cl.
CPC ............... *F16K 24/00* (2013.01); *A61M 5/162* (2013.01); *F16L 29/005* (2013.01)

(58) Field of Classification Search
CPC . A61M 5/3202; A61M 5/1782; A61M 5/162; F16L 29/00; F16L 29/005; F16L 29/02; F16K 24/00

USPC ......... 137/318; 251/149.1; 604/411, 412, 415
See application file for complete search history.

(56) References Cited

U.S. PATENT DOCUMENTS

| 2,770,234 | A | * | 11/1956 | Nesset et al. ................... 604/405 |
| 3,993,068 | A | * | 11/1976 | Forberg ......................... 604/251 |
| 4,022,258 | A | | 5/1977 | Steidley |
| 4,576,594 | A | | 3/1986 | Greenland |
| 5,466,220 | A | | 11/1995 | Brenneman |
| 5,562,616 | A | | 10/1996 | Haber et al. |
| 6,706,031 | B2 | * | 3/2004 | Manera .......................... 604/411 |
| 7,540,863 | B2 | * | 6/2009 | Haindl ........................... 604/414 |
| 7,703,486 | B2 | * | 4/2010 | Costanzo ....................... 141/346 |
| 2002/0087144 | A1 | | 7/2002 | Zinger et al. |
| 2002/0104584 | A1 | | 8/2002 | Spero et al. |
| 2004/0249341 | A1 | * | 12/2004 | Newbrough et al. ........... 604/87 |

FOREIGN PATENT DOCUMENTS

| DE | 26 47 624 A1 | 5/1977 |
| EP | 1 165 011 B1 | 1/2002 |

(Continued)

*Primary Examiner* — Kevin Lee
(74) *Attorney, Agent, or Firm* — Nath, Goldberg & Meyer; Jerald L. Meyer (57) ABSTRACT

A device is placed upon a container that is sealed by a sealing element and filled with a liquid, the device allowing the liquid to be withdrawn. The device is provided with a penetration element with a hollow needle that is held in an unused position on a head section. The penetration element is held by guide elements on the head section so that the element can be pressed against the sealing element in a withdrawal position, in which the hollow needle penetrates the sealing element. At least one aeration channel is provided to equalize the pressure in the container during the withdrawal of the liquid, the channel running preferably along the hollow needle. The air sucked from the atmosphere enters the aeration channel via a filter. This prevents the contamination of the liquid and the latter can be withdrawn without the risk of a reverse flow.

18 Claims, 11 Drawing Sheets

(56) References Cited

FOREIGN PATENT DOCUMENTS

| FR | 2 753 624 | 3/1998 |
| WO | 98/19724 A1 | 5/1998 |
| WO | 01/00261 A1 | 1/2001 |
| WO | 01/60436 A1 | 8/2001 |
| WO | 03/064907 A1 | 8/2003 |
| WO | 2008/126090 A1 | 10/2008 |

* cited by examiner

DEVICE FOR WITHDRAWING LIQUID FROM A CONTAINER

This is a National Phase Application filed under 35 U.S.C. 371 as a national stage of PCT/EP2011/072716, filed Dec. 14, 2011, and claims priority from European Application No. 10195706.6, filed Dec. 17, 2010, the content of each of which is hereby incorporated by reference in its entirety.

BACKGROUND OF THE INVENTION

The invention relates to a device for withdrawing a liquid from a container according to the preamble of claim 1. Here, devices for needle-free withdrawal of pharmaceutical substances from a hermetically sealed glass vessel are generally concerned. Here, the liquid can be transferred into an injection syringe, wherein the needle is only fitted subsequently. Of course, devices of this type can also be used in the non-medical field however, for example for chemical analysis purposes in the food processing field, etc.

A generically comparable device is known by WO 01/60436, in which a linearly displaceable piercing tip is held in a tubular housing, which is fitted onto the closed container mouth. The piercing tip is fixed in the above idle position by flexible detent catches and has a circumferential toothing, which engages in corresponding lateral tooth segments. In the event of application of a pressure from above in the direction of the container once a syringe has been attached, the piercing tip releases from the latched connection and slides downwardly in the toothing in a manner fixed against rotation until the sealing plug on the container has been pierced. The container content can then be aspirated by means of the injection syringe.

A significant disadvantage of known devices lies in the fact that, even once the sealing element has been pierced by the hollow needle, the interior of the container is sealed with respect to the atmosphere when another container, such as an injection syringe, is attached to the penetration element. As the liquid is aspirated from the container, a negative pressure is thus produced, which in extreme cases causes the majority of the liquid to flow back into the container as soon as the pump movement is interrupted. Due to the flexibility of the sealing element, air may flow along the outer face of the hollow needle with a strong negative pressure in the container. This is undesirable however because microbiological impurities can thus infiltrate the container and therefore the liquid.

SUMMARY OF THE INVENTION

One object of the invention is therefore to create a device of the type mentioned in the introduction, with which the aforementioned disadvantages are avoided and with which a backflow of liquid into the container is avoided, in particular whilst maintaining sterile conditions. The device should also function reliably and should also be easy to operate by individuals not trained specifically for this purpose. In addition, it should be possible to produce the device in a simple and cost-effective manner, since the device is a component of a disposable packaging that has to be disposed of after use.

These objects are achieved in accordance with the invention by a device having the features in claim 1. The at least one aeration channel running preferably along the hollow needle evidently causes the interior of the container to be short-circuited to the atmosphere in the withdrawal position. The build-up of a continuously increasing negative pressure in the container is thus avoided, since as much air flows into the container as liquid is withdrawn. In spite of this, a dirt-free and even germ-free environment in the container is ensured when, in accordance with a further embodiment, the fed air has to pass a filter. Depending on the nature of this filter, the smallest of particles or living beings can also be retained. Of course, it is conceivable to arrange a plurality of aeration channels and for these to extend along the hollow needle linearly or also helically. The arrangement of an aeration channel on an element separate from the hollow needle, for example in the form of a separate aeration needle, would also be conceivable.

The aeration channel is particularly advantageously formed however as a groove on the outer face of the hollow needle. There are preferably a plurality of parallel grooves. A component of this type can be easily produced, and, with sufficient groove depth, a sufficiently large passage cross section is kept clear, even if the sealing element consists of very soft and resilient material.

The filter can be arranged fundamentally on the penetration element and can be displaced together therewith, or it may be held rigidly on the head piece. It is important in this case that the side of the filter facing towards the aeration channel is a component of a chamber that is delimited in a sterile manner with respect to the atmosphere. The filter may for example be arranged on the penetration element, preferably at the atmosphere-side end of the aeration channel, for example more specifically on a collar that surrounds the hollow needle, is provided with openings and simultaneously supports or carries the filter. This variant arranged close to the aeration channel has the advantage that the area of the filter can be kept relatively small.

With an assignment of the filter on the head piece, the arrangement is preferably provided in a region facing towards the sealing element. Here, the filter may be arranged in a mount, which surrounds the penetration element in an annular manner. This arrangement has the advantage that the space to be kept sterile in the idle position can be kept very small.

Further advantages can be achieved if the guide means comprise at least one wall portion, which connects the penetration element to the head piece and holds said penetration element in the idle position, wherein the wall portion is deformable in such a way that it guides the penetration element until the withdrawal position is reached. Due to the fixed connection between the head piece and the penetration element, an anti-rotation lock is ensured and good straight-line guidance is also produced as a result of the deformability. An embodiment of this type of the guide means would also be very advantageous on conventional devices without an aeration channel and without a filter.

The deformable wall portion may for example be at least one resilient membrane surrounding the penetration element. This membrane may be deformable in such a way that it fixes the penetration element in the withdrawal position under the spring bias. As a result of its spring properties, the dome-like membrane is thus biased both in the idle position and in the withdrawal position. Here, the "clicker" effect of the membrane is utilized. Of course, detent means may also be provided however in order to fix the penetration element in the withdrawal position, such that the spring bias of the membrane is irrelevant for maintaining the withdrawal position.

The membrane can be formed rather differently and for example may also consist in the circumferential direction of a plurality of separate segments.

Atmospheric air can flow via the gaps between the segments in the withdrawal position. It is also conceivable however for a membrane closed in the idle position to be provided with predetermined breaking points, which rupture when the penetration element is transferred into the withdrawal position. Predetermined breaking points of this type have the advantage that the membrane is relatively dimensionally stable in the idle position and only has increased elasticity once the predetermined tearing lines have ruptured. In addition, air from the atmosphere can also flow here via the ruptured predetermined tearing lines in the withdrawal position.

Alternatively, the guide means may also have at least two webs however, which form the aforementioned wall portions and of which each is provided with at least one bending joint in such a way that the webs can be folded together as the penetration element is displaced into the withdrawal position. The webs thus form spider-like legs of the penetration element, which can preferably fold outwardly during the course of the linear movement.

Alternative embodiments of the guide means would of course be conceivable. For example, the wall portion could thus also be formed as a bellows, which can be pressed together in the manner of an accordion. A number of interconnected rings or ring segments, which can be pushed together telescopically, would also be conceivable. A considerable advantage is in any case achieved when the guide means are connected in one piece to the head piece and/or to the penetration element. The entire structure can thus be produced in one piece as an injection-molded part in plastic material. In specific cases, it may also be conceivable however due to the fabrication method to produce individual components separately and to then weld or otherwise connect said components to one another.

For example, in an embodiment that is possibly likewise to be preferred, the guide means may comprise fastening means, which, in order to connect the guide means to the head piece, can be latched thereto. The latched connection is preferably implemented here in such a way that the two parts are interconnected non-releasably, that is to say are not intended to be released by a user. For example, the fastening means may comprise detent hooks, which engage in corresponding detent recesses on the head piece, where they are then latched. Here, the guide means can be connected for example in one piece to the penetration element or can be connected thereto via further fastening means. Of course, depending on the requirement, other connection types are also conceivable, with which the guide means are connected to the head piece, for example by means of laser welding or ultrasonic welding or also by adhesive bonding however.

An embodiment of the penetration element with differently formed head pieces can therefore be used. For example, different head pieces can be matched to different containers, whereas identical penetration elements can be connected to the head pieces by means of the aforementioned fastening means. In addition, different material properties can thus be paired with one another in an optimal manner. Here, materials that can be sterilized by means of different methods (for example that can be sterilized by means of irradiation or steam) without enduring damage during this process are optimal.

The head piece may advantageously also be formed in two or more parts, wherein a first part is provided to be coupled to the container and a second part is connected to the penetration element. This results in the advantage that, for example, one embodiment of the second part can be used for different designs of the first part, for example for different containers. The at least two parts are preferably interconnected via latched connections or for example via a welded connection by means of laser or ultrasound or via an adhesive bond. In principle, one-piece embodiments of the head pieces may also be advantageous however.

In order to ensure a germ-free and an as air-tight or liquid-tight attachment as possible to the penetration element, said penetration element is provided with a corresponding coupling part. Here, this may be the female taper of a Luer lock for example. Other types of coupling means, such as any snap-fit seals or the like, are also conceivable however.

The penetration element may additionally comprise detent means, by means of which it can be latched in the withdrawal position. It is thus ensured that no undesired relative movements occur as the liquid is withdrawn.

These detent means are preferably arranged on the penetration element in such a way that they are externally accessible for manipulation by a user. A latched connection can therefore be produced manually as necessary, should this not occur duly automatically for example. In particular, the detent means may be arranged outside the deformable wall portion formed for example as a membrane. The penetration element preferably comprises a fingerplate, which is provided for displacement between an idle position and withdrawal position. Here, the fingerplate forms a support for a user's finger so as to easily carry out the transition from the idle position into the withdrawal position. The detent means may advantageously be formed on the fingerplate, for example in the form of detent hooks or detent tongues extending towards the head piece.

The head piece in this case preferably comprises detent means, which are complementary to the detent means of the penetration element such that the penetration element can be latched by means of its detent means to the head piece. In the withdrawal position, the head piece and penetration element therefore form a well-fixed and robust arrangement. It goes without saying that, in variants, the penetration element can also be latched elsewhere in the withdrawal position, for example directly on the flange of an attached container. A latched connection cannot be controlled as well in this way however, since it is not produced within the device alone.

The head piece may carry a centering ring, which additionally guides and centers the hollow needle. The sealing element is thus pierced at a precisely defined point. In addition, undesired transverse movements caused by incorrect handling during the piercing process are avoided.

To protect the penetration element in the idle position and also as a security assurance, the penetration element is covered by a releasable protective cap. This protective cap must be sufficiently stable so as to prevent displacement of the penetration element, even under severe impacts and shocks. As a security assurance, the protective cap may comprise a separable guarantee band for example. The protective cap additionally also has the further object of sealing the device in a germ-free manner. This requires the protective cap to be pressed tightly against the sealing element and/or against the container mouth. This can be achieved for example via a sleeve, which is shrunk-fit or pressed on or flange-mounted around the head piece and around the container mouth. With an embodiment of this sleeve for example formed from aluminum or from an aluminum alloy, one end of the sleeve can be cast directly into the head piece during production. Once the container has been filled and sealed, the free end can be pressed on or flange-mounted around the container mouth.

The protective cap can particularly advantageously also be provided with a thread and screwed onto the head piece and/or onto the penetration element. The screw cap could be fixed for example via a welded connection.

A very advantageous possibility for fastening on a container mouth also lies in snapping the head piece onto the container mouth. With accordingly formed detent means, a relatively high contact pressure can be built up in this case. Comparable snap-fit connections on container mouths are already known for example in the case of seals in the food processing industry.

A further very advantageous embodiment lies in the selection of maximally transparent plastics for the individual components. The finished filled and assembled product can therefore be inspected visually for any defects without destruction.

It has been found that a plastic having a certain proportion of glass balls or of a glass granulate is particularly advantageous. It has been found that a proportion of 5%-20%, preferably 10%-15%, produces particularly good properties with regard to stability, in particular in the idle position, and also with regard to the fracture or tear behavior of the membrane during the transition into the withdrawal position E.

BRIEF DESCRIPTIONS OF THE DRAWINGS

Further advantages and individual features of the invention are presented in the drawings and will be described hereinafter. In the drawings.

DETAILED DESCRIPTION OF THE INVENTION

Figure 1:
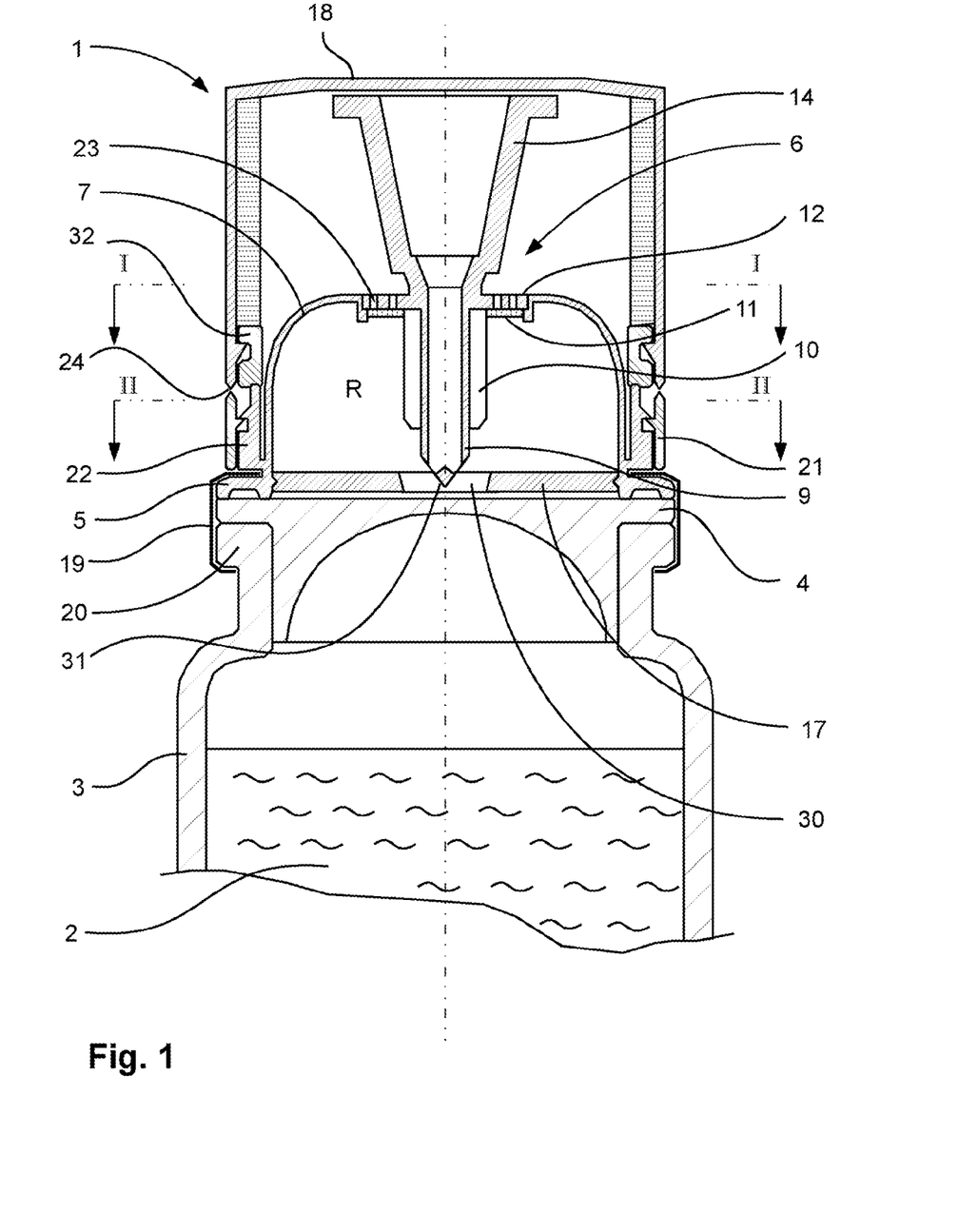
FIG. 1: shows a considerably enlarged cross section through a device according to the invention in the idle position.

FIG. 1 shows an arrangement consisting of a device 1 according to the invention, which is fitted onto the container mouth 20 of a container 3. The container 3 is fabricated for example from glass, is filled with a liquid 2, and is sealed in an airtight manner by means of a sealing element 4, for example made of rubber. The liquid 2 may be a pharmaceutical active ingredient, which is intended to be injected by means of an injection syringe either directly into the human or animal body or to be admixed with an infusion system.

The device 1 consists substantially of a head piece 5 made of plastic material, which rests tightly via its underside on the outer edge region of the sealing element 4 and which is connected via a membrane 7 curved in a dome-like manner to a central penetration element 6. The head piece 5 is connected in one piece to a wall portion 22, which is used as a support for an externally arranged guarantee band 21. The sealing and interlocked connection of the head piece 5 to the container mouth 20 is achieved via a sleeve 19 made of aluminum, which is cast directly into the head piece 5 and which is pressed at its free end onto the container mouth 20. In a plane immediately above the sealing element 4, the head piece carries a centering ring 17, which has a central opening 30 and which for example can be snapped into place.

Figure 3:
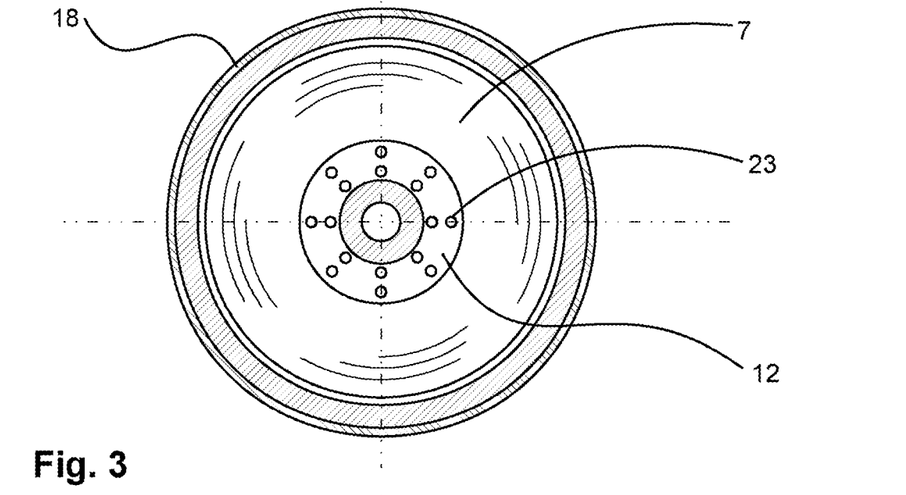
FIG. 3: shows a section through the plane I-I according to FIG. 1, FIG. 4: shows a section through the plane II-II according to FIG. 1, FIG. 5: shows a cross section through an alternative exemplary embodiment of a device.

The preferably rotationally symmetrical penetration element 6 has, in the central portion, a circumferential collar 12, in which aspiration openings 23 are arranged (FIG. 3). A microbiologically tight filter 11, which covers all aspiration openings 23, is arranged beneath the collar. The female taper of a Luer lock 14 is arranged integrally above the collar 12. Said female taper transitions directly into a hollow needle 9, which extends downwardly beneath the collar 12 and which opens out into a piercing tip 31 provided with openings. The term "hollow needle" is used here for any element that forms an aspiration channel and that is able to penetrate the sealing element 4.

Figure 4:
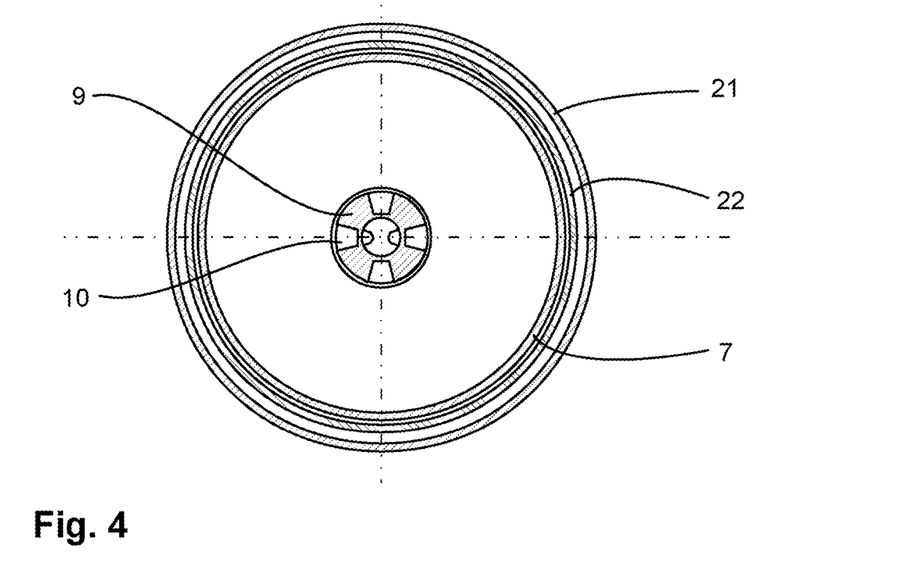

As can also be seen in particular from FIG. 4, the hollow needle 9 has a relatively thick wall, along which aeration channels 10 in the form of grooves are preferably arranged in parallel. These grooves extend until directly below the collar 12. The entire penetration element 6 is preferably formed in one piece, apart from the filter 11. It can be welded or snapped into the membrane 7, or it may likewise even be formed in one piece therewith. The aeration channels can also be formed in cross section in the manner of a dovetail groove. The risk of the resilient material of the sealing element 4 sealing the aeration channels can thus be reduced.

The membrane 7 is resilient, such that it biases the penetration element 6 upwardly in the illustrated idle position R. In this idle position, the penetration element is covered by a protective cap 18, which is connected via a predetermined breaking line 24 to the guarantee band 21. A ring seal 32 between the wall portion 22 and the protective cap 18 ensures that the entire interior of the protective cap is sealed hermetically and in a sterile manner above the sealing element 4. The protective cap 18 can be fabricated from plastic material or also from aluminum. In specific cases, it would be conceivable for the Luer lock 14 to be held or centered in the idle position R by the protective cap 18.

The withdrawal of the liquid from the container 3 in the withdrawal position E will be explained hereinafter with reference to FIG. 2. Before the withdrawal position is reached, the protective cap 18 has to first be removed such that only the guarantee band 21 still remains on the head piece 5. Depending on the guarantee system, the guarantee band could also be removed when opening the protective cap. Immediately once the protective cap has been removed, the male taper 26 of a syringe 25 is introduced into the Luer lock 14 and a force is exerted onto the penetration element 6 in the arrow direction k. In so doing, the hollow needle 9 penetrates the sealing element 4, such that the piercing tip 31 protrudes into the interior of the container 3. Here, the aeration channels 10 additionally create a connection between the interior of the container 3 and the inner face of the membrane 7.

In the withdrawal position E, the membrane 7 is curved severely in the direction of the sealing element in such a way that the spring bias changes the direction of force and fixes the penetration element in the withdrawal position. The friction between the hollow needle 9 and the sealing element 4 also contributes to the fact that the penetration element remains in this position.

The liquid is actually withdrawn by drawing the syringe 25, not of course in the illustrated position, but with the head arranged upwardly, such that the liquid floods the inner face of the sealing element 4. By drawing the syringe, the liquid thus flows in the arrow direction f through the hollow needle 9 into the syringe 25. The negative pressure produced during this process above the liquid level is counterbalanced by air aspirated from the atmosphere, which reaches the container 3 in the arrow direction 1 via the intake openings 23, through the filter 11 and via the aeration channels 10. A contamination of the liquid is not possible here, because dirt particles or for example also bacteria are filtered out at the filter 11.

Figure 2:
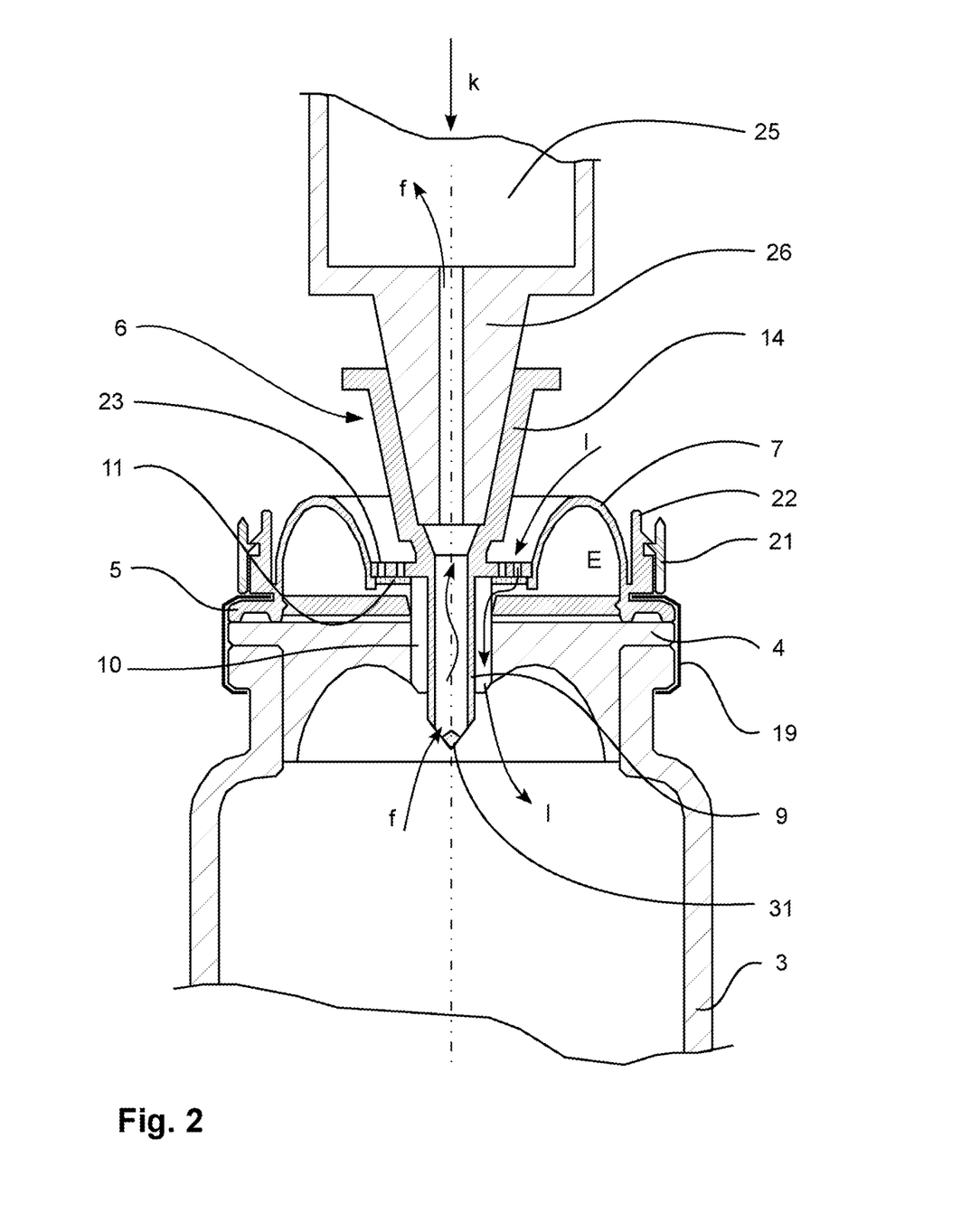
FIG. 2: shows the device according to FIG. 1 in the withdrawal position with attached syringe.
Figure 5:
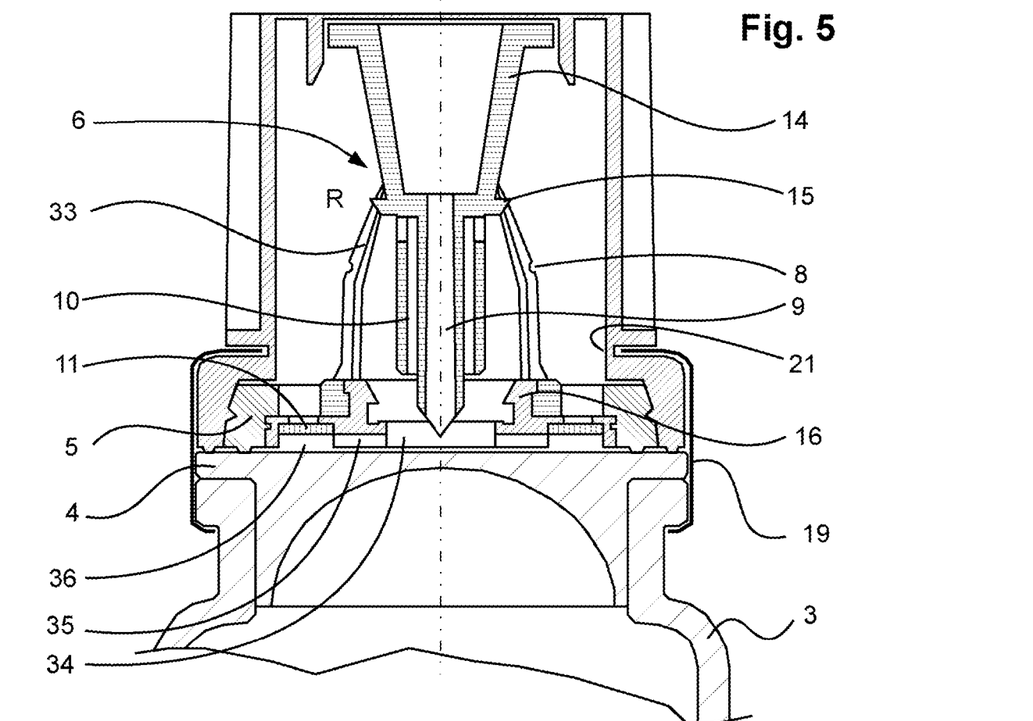
Figure 6:
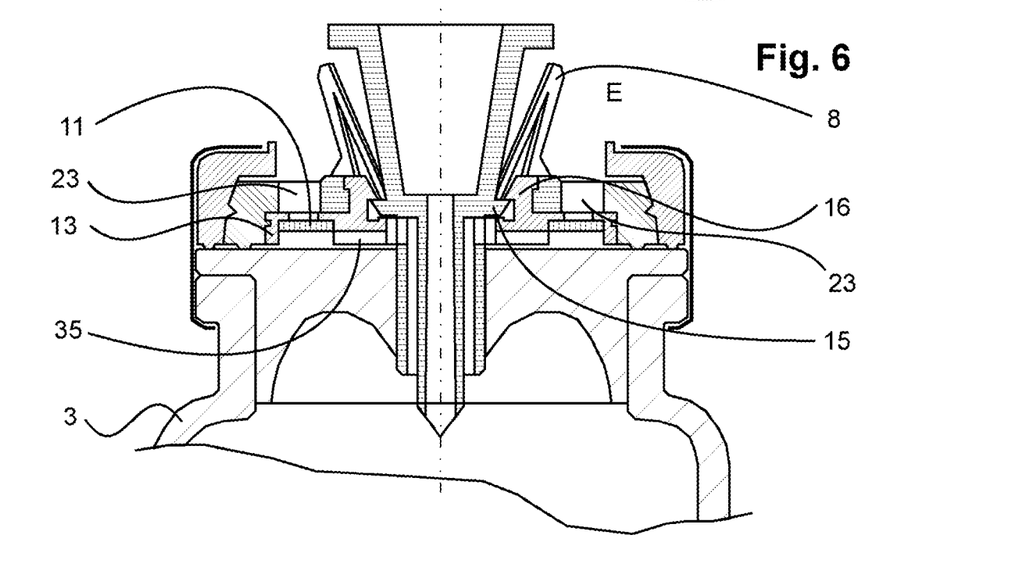
FIG. 6: shows the device according to FIG. 5 in the withdrawal position.

An alternative exemplary embodiment of a device is illustrated in FIGS. 5 and 6, wherein identical components are provided with reference signs identical to those used in the exemplary embodiment according to FIGS. 1 and 2. The main difference lies on the one hand in the connection between the head piece 5 and the penetration element 6 and on the other hand in the arrangement of the filter 11. The sealing cap 18 is designed slightly differently and is not provided with a separate guarantee band. Rather, the predetermined breaking line 24 is located directly above the cast-in upper edge of the sleeve 19.

The head piece 5 is connected to the penetration element 6 via four material webs 8, which are distributed uniformly around the hollow needle 9. Each material web has at least one bending joint 33. The material webs 8 thus form spider-leg-like supports, which hold the penetration element 6 in the idle position. The Luer lock 14 is additionally fixed on the base of the sealing cap 18.

In the present exemplary embodiment, the filter 11 is not fixed on the penetration element, but on the head piece 5. To this end, a separate filter mount 13 is provided, which has a central opening and which surrounds the hollow needle 9 in an annular manner. The inner, hub-like part of the filter mount rests on the sealing element 4, wherein the central opening 34 however is connected via grooves 35 to the annular hollow chamber 36, in which the filter 11 is fixed. An inwardly protruding detent ring 16 is arranged on the filter mount 13. An outwardly protruding detent ring 15 is also arranged on the penetration element 6.

In the withdrawal position according to FIG. 6, the material webs 8 are folded about the bending joints 33 and in so doing protrude slightly outwardly. The detent rings or detent lugs 15 and 16 are latched to one another and thus fix the penetration element, of which the hollow needle 9 has pierced the sealing element 4. Air from the atmosphere passes through the filter 11 via the grooves 35 and the aeration channels 10 into the interior of the container 3.

Figure 7:
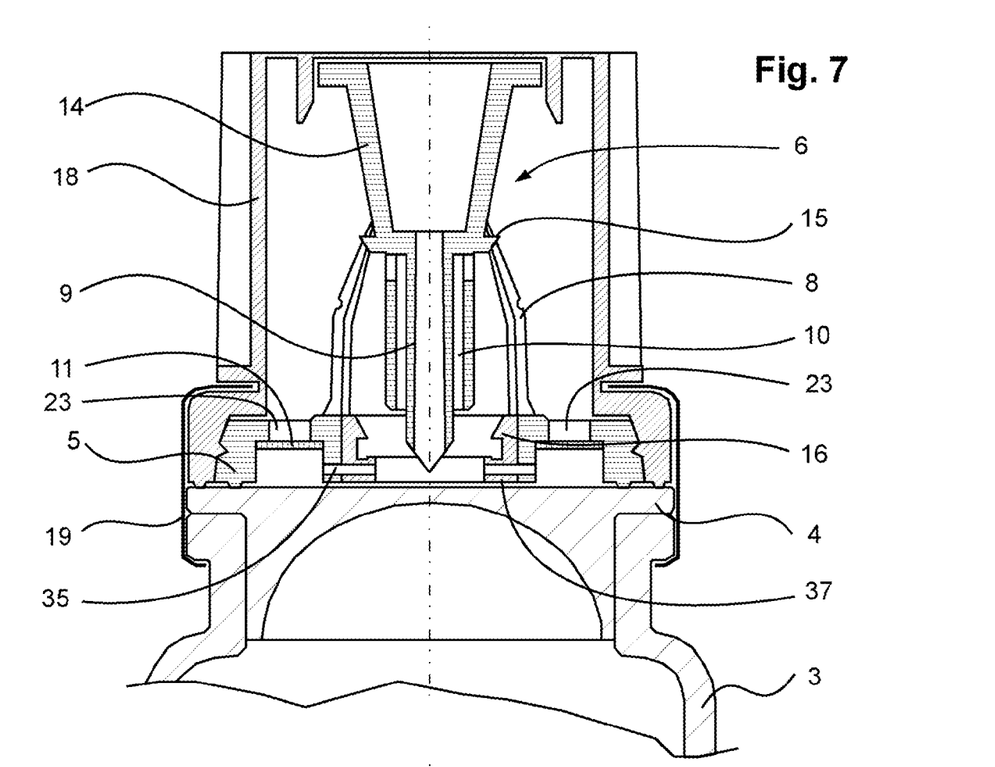
FIG. 7: shows a further slightly modified exemplary embodiment of the device according to FIG. 5, FIG. 8: shows the device according to FIG. 7 in the withdrawal position.
Figure 8:
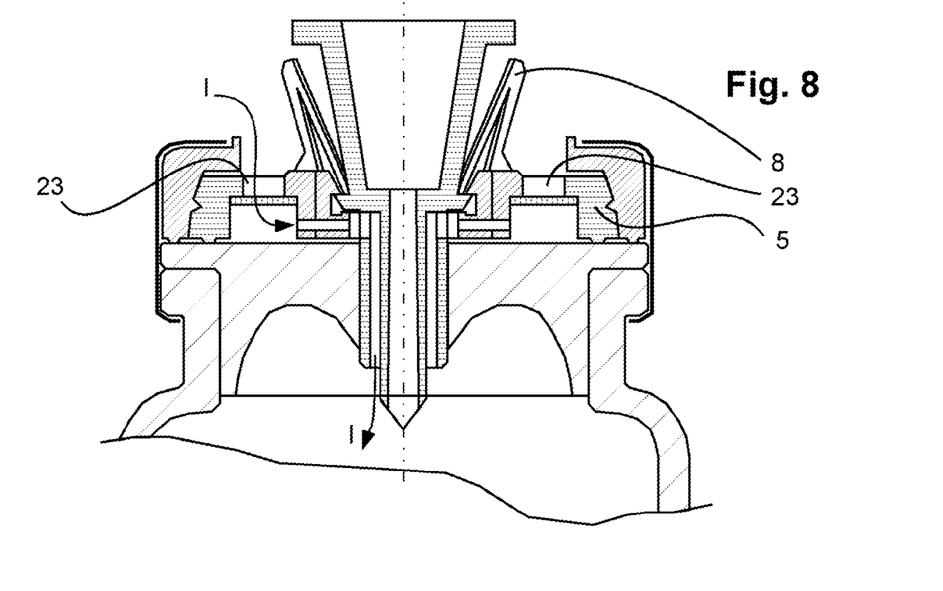

The exemplary embodiment according to FIGS. 7 and 8 differs from that according to FIGS. 5 and 6 merely by the manner in which the filter 11 is fixed. Here, the filter is not fixed by a separate filter mount, but directly by a portion of the head piece 5. Here, merely an inner ring 37, which carries the inwardly protruding detent ring 16, is formed separately.

Figure 9:
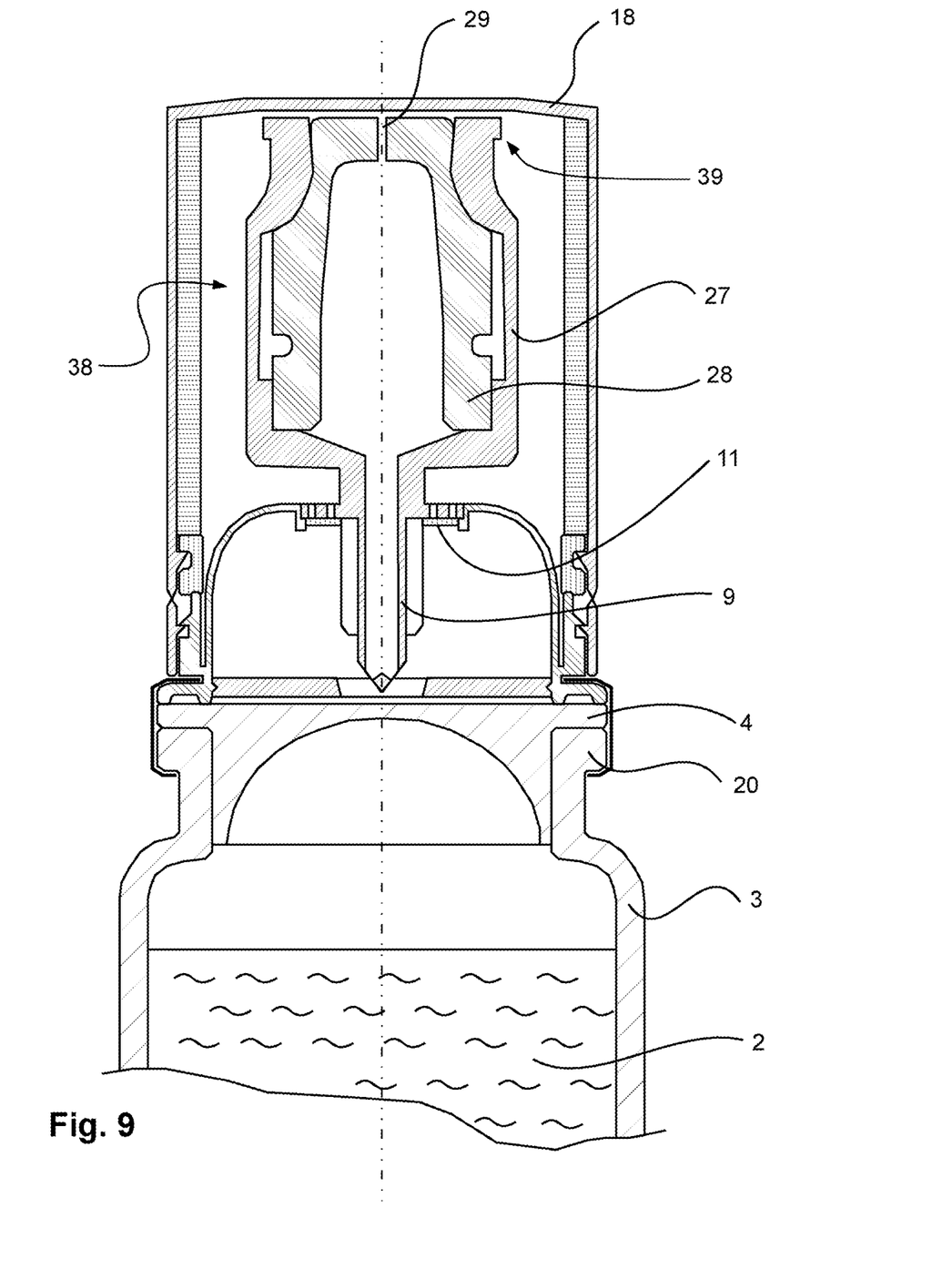
FIG. 9: shows a cross section through a device according to the invention with integrated withdrawal valve.

The exemplary embodiment according to FIG. 9 corresponds largely to that according to FIG. 1. A valve denoted by 38 is incorporated in the special coupling part 39 formed by a valve housing 27. Said valve makes it possible, in the withdrawal position, to withdraw liquid from the container 3 in a number of chronologically separate sequences, wherein a sterile seal is ensured after each withdrawal. A valve body 28 made of a flexible material is mounted in the valve housing 27. In this valve body, a slit 29 is arranged, which is closed in the idle state such that the valve body 28 acts as a seal. When a syringe is fitted into the Luer lock 39, the slit 29 is spread open and thus releases the access to the hollow needle 9. A valve of this type is described for example in WO 03/064907. Due to the greater overall height of the penetration element 6, the sealing cap 18 must of course also be longer.

Figure 10:
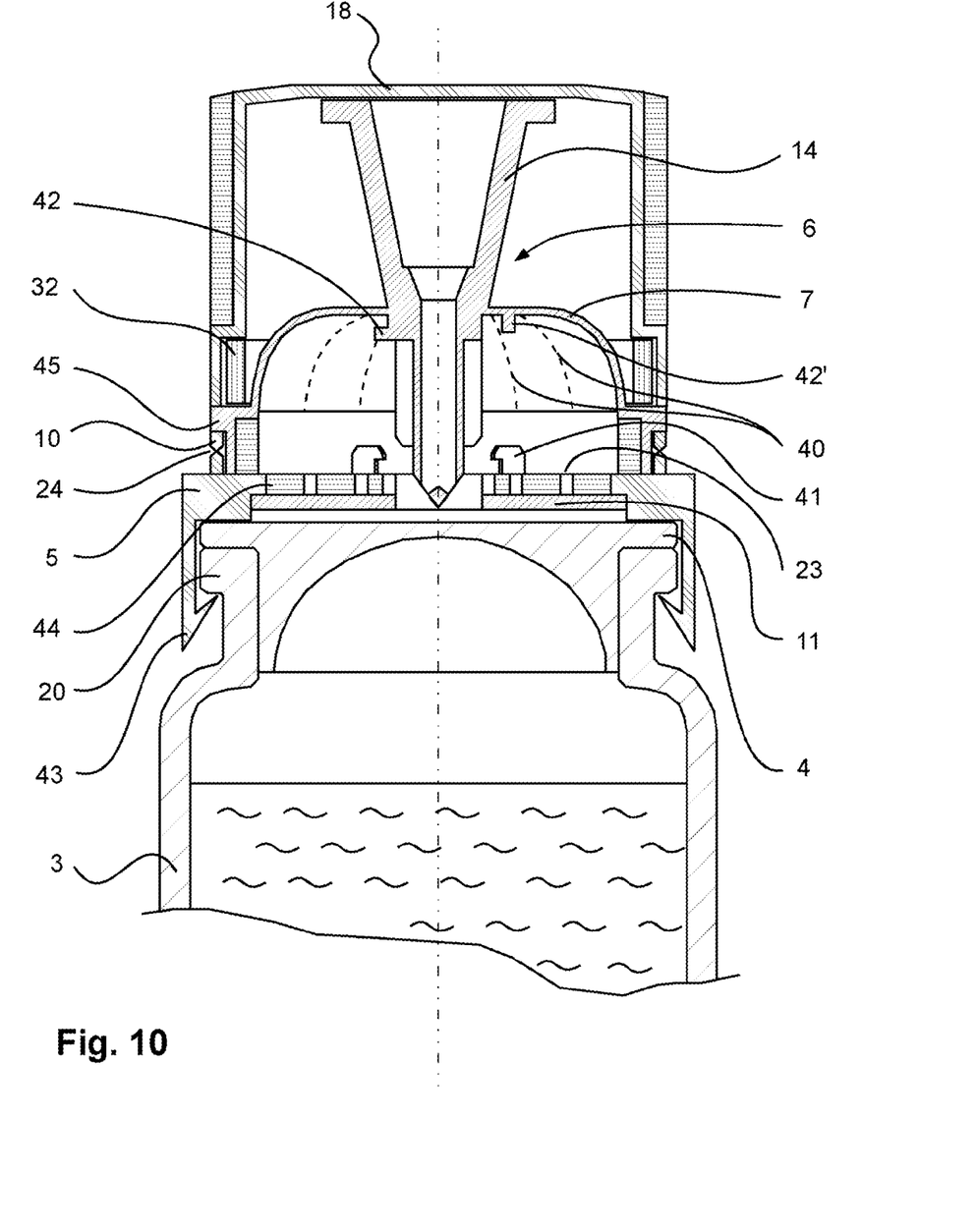
FIG. 10: shows a cross section through a further exemplary embodiment of a device.

The exemplary embodiment according to FIG. 10 indeed has a certain similarity to that according to FIG. 1, but differs therefrom by the design of the membrane 7, the arrangement of the filter 11, and also the type of fastening on the container mouth 20. In addition, the penetration element 6 is fixed in the withdrawal position by a detent connection. The membrane 7 curved in a dome-like manner is provided with predetermined breaking points or predetermined breaking lines 40 distributed over the circumference, which extend approximately parallel with respect to the longitudinal center axis from the zenith of the dome as far as the lower edge thereof. These predetermined breaking points can be formed here as weakened lines or may also be perforations. As the penetration element is transferred from the illustrated idle position into the withdrawal position (similarly to FIG. 2), the predetermined breaking points 40 rupture, thus producing slit-like openings. In the withdrawal position, detent blocks 42 arranged on the penetration element latch into the detent hooks 41 on the head piece 5 and thus fix the withdrawal position. The detent blocks can be designed rather differently, and, for example as illustrated in the left-hand half of the image, may be arranged rigidly on the penetration element. An arrangement on the membrane 7, as illustrated in the right-hand half of the image (42'), is also conceivable however, wherein each detent block carries out a pivoting movement of approximately 90° until reaching the corresponding detent hooks 41.

The head piece 5 is not fixed here on the container mouth by means of a sleeve, but is snapped thereonto with the aid of a snap-fit collar 43. This snap-fit collar is dimensioned in such a way that a sealing pressure is exerted onto the sealing element 4 and a removal of the protective cap 18 is also possible without the head piece 5 being lifted accidentally from the container 3.

The filter 11 is assigned here to the head piece 5, wherein it is fastened directly beneath a carrier plate 44 provided with intake openings 23. The flowing air thus flows via the opened predetermined breaking points 40, through the intake openings 23 and the filter 11 and then via the aeration channels 10 into the interior of the container 3.

In the case of the present exemplary embodiment, the protective cap 18 with the predetermined breaking line 24 is also designed in a slightly modified manner. The dome-like membrane 7 transitions at its lower edge into a circumferential support ring 45, which for example is connected in one piece to the head piece 5 by means of a welded connection. A seal 32, which hermetically seals the inner face of the protective cap 18 outwardly, is supported on said support ring. The ring seal 32 could also be integrated as a bi-component injection-molded part directly into the protective cap 18. The material strip beneath the predetermined breaking line 24 is designed as a guarantee band, after the removal of which the protective cap 18 can be lifted from the support ring 45.

FIGS. 11 to 14 show various views of an alternative exemplary embodiment of a penetration element 6 of a device according to the invention and are described together hereinafter. Here, identical components are provided with reference signs identical to those used in the exemplary embodiments according to the previous figures. The exemplary embodiment in FIGS. 11 and 12 (and also 13 and 14) corresponds in large parts to the device illustrated in FIG. 10. A significant difference lies in the design of the membrane 7, which is provided for connection of the penetration element 6 to the head piece 5, and also in the design of detent elements for latching the penetration element 6 to the head piece 5 in the withdrawal position.

The membrane 7 is likewise formed in a dome-like manner and transitions at the edge via a support ring 45 into a fastening ring 56, which is provided to fasten the membrane 7 on the head piece 5. To this end, the support ring 45 has four detent hook pairs 54, which are arranged on the end face and are provided for latching into corresponding recesses 63 of the head piece 5 (see FIGS. 15-18).

Figure 11:
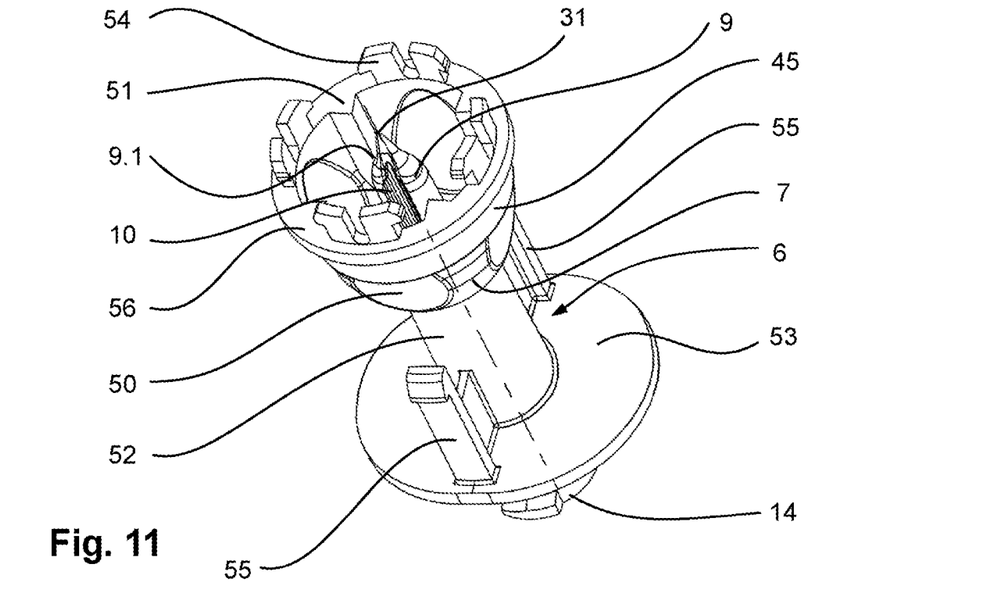
FIG. 11: shows an external oblique view of a further exemplary embodiment of a device in an idle position without head piece.
Figure 12:
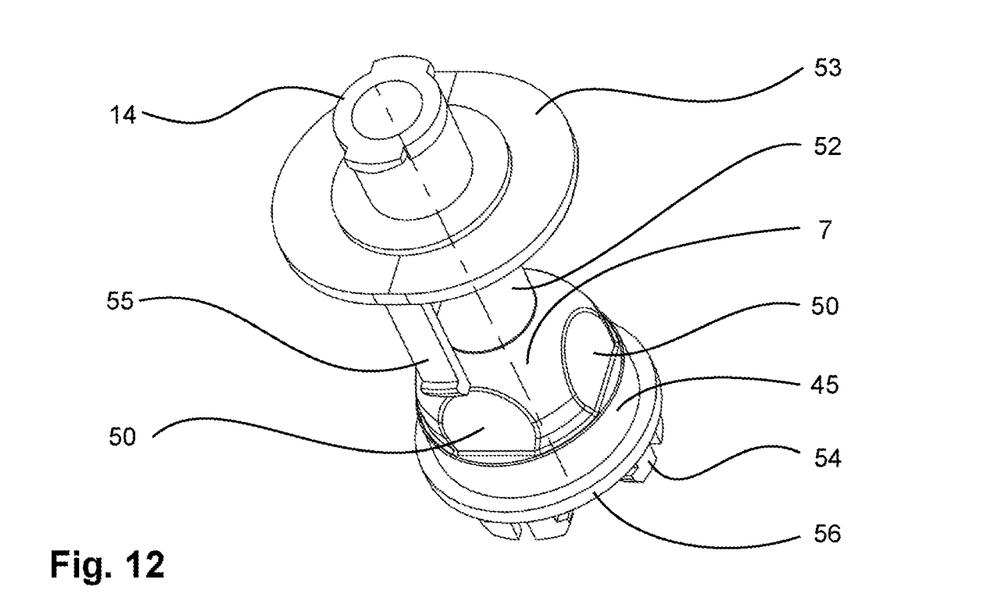
FIG. 12: shows a further external oblique view of the exemplary embodiment according to FIG. 11, FIG. 13: shows a detailed view of a hollow needle of the exemplary embodiment according to FIG. 11, FIG. 14: shows an external side view of the exemplary embodiment according to FIG. 11, FIG. 15: shows an external side view of a head piece for the device in FIG. 11, FIG. 16: shows a plan view of the head piece according to FIG. 15, FIG. 17: shows a longitudinal section through the head piece according to FIG. 15, FIG. 18: shows a further longitudinal section through the head piece according to FIG. 15, FIG. 19: shows a longitudinal section through a further embodiment of a two-part head piece for a device according to the invention.
Figure 13:
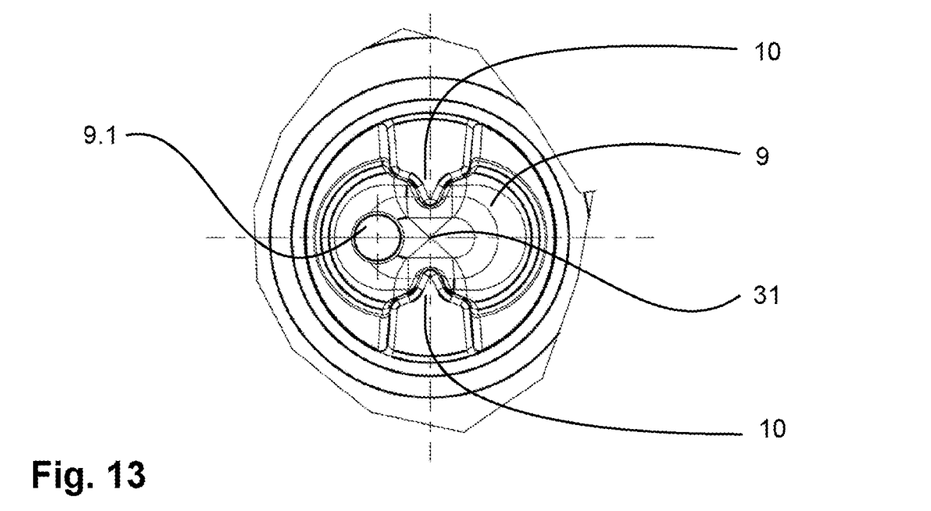
Figure 14:
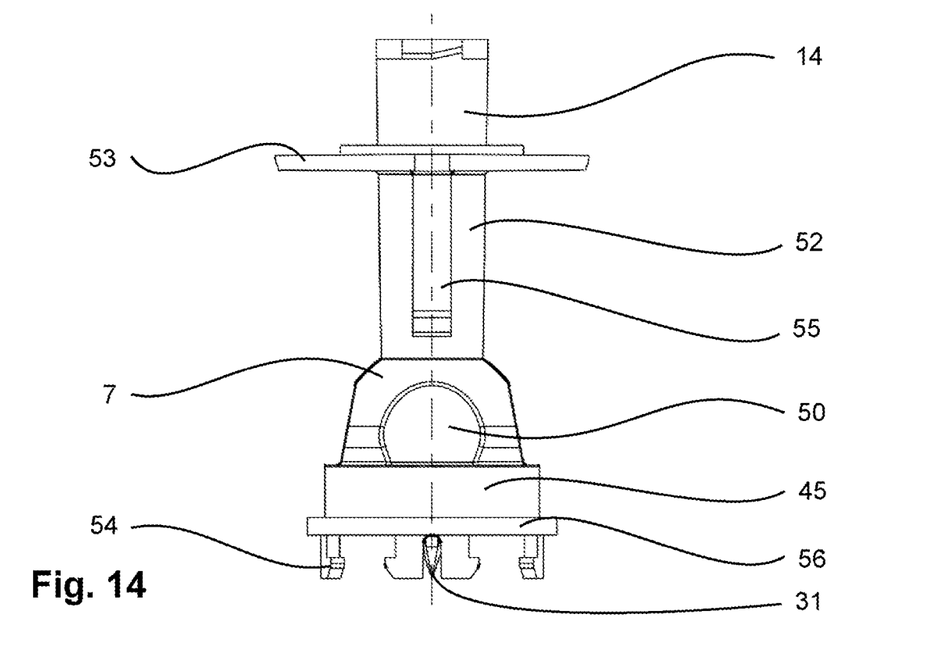
Figure 15:
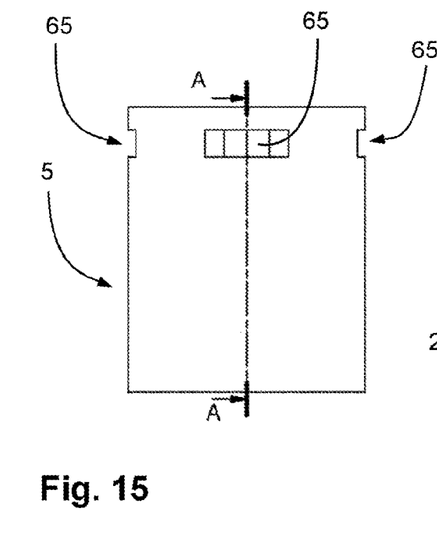
Figure 16:
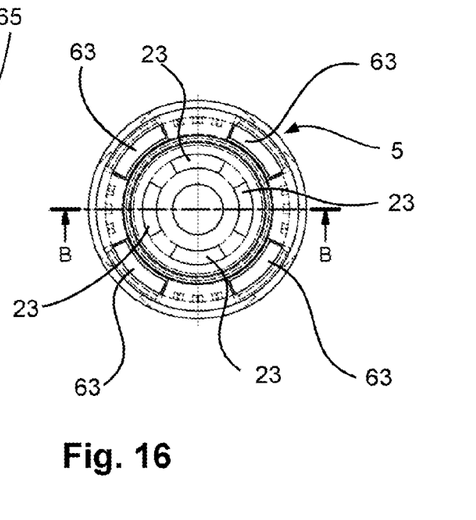
Figure 17:
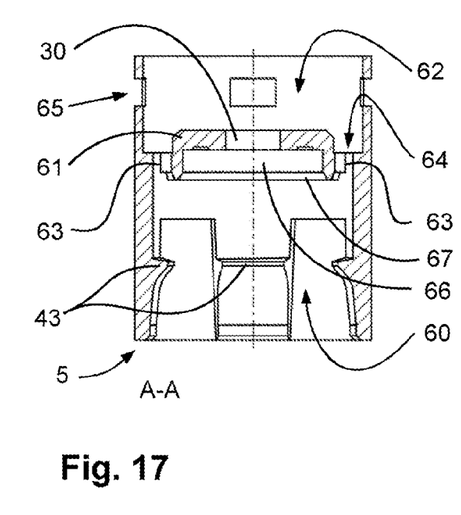
Figure 18:
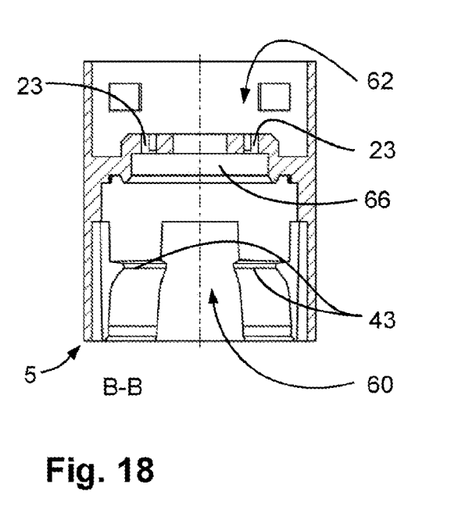

The membrane 7 has four substantially circular flattened portions 50, which for example may be defined by a predetermined breaking point. On the inner wall, the membrane 7 has four perforation webs 51, which are arranged substantially in the longitudinal direction between the circular flattened portions 50. The perforation webs 51 are stiff and are connected rigidly to the support ring 45 and also to the fastening ring 56. As the penetration element 6 transitions into the withdrawal position E, the perforation webs 51 tear or perforate the membrane 7. It is thus ensured that external air can be fed to the aeration channels 10 of the hollow needle 9 of the perforation element 6.

A substantially circular cylindrical neck 52 of the penetration element 6 adjoins the membrane 7 and extends outside the membrane 7 in the longitudinal direction. At the end, the neck 52 transitions into the Luer lock 14. A fingerplate 53 projects in a flange-like manner between the neck 52 and Luer lock 14, transversely with respect to the longitudinal direction of the penetration element 6. Here, an area of the fingerplate 53 is larger than an outline of the membrane 7, such that, in a plan view in the longitudinal direction, the overall membrane 7 with support ring 45 and fastening ring 56 is covered by the fingerplate 53.

The Luer lock 14 is connected via a fluid channel in the neck 52 to a withdrawal channel 9.1 of the hollow needle 9 of the penetration element 6, said hollow needle being arranged centrally within the membrane 7. Here, the hollow needle 9 has two aeration channels 10 in the form of V-shaped longitudinal grooves, which are arranged on the outer face of the hollow needle 9 in a mutually opposed manner with respect to the longitudinal axis. Here, the withdrawal channel 9.1 of the hollow needle 9 is arranged off-center, such that a piercing tip 31 can be formed solidly for good penetration ability (see also FIG. 13).

Two detent tongues 55 arranged in a mutually opposed manner with respect to the longitudinal direction are formed on the fingerplate 53 in a manner extending in the longitudinal direction towards the membrane 7. Here, the detent tongues 55 are used to latch the penetration element 6 in the withdrawal position E in corresponding recesses 65 on the head piece 5 (see FIGS. 15 to 18). The detent tongues 55 (with respective recesses on the head piece 5) therefore perform a similar function to, for example, the detent blocks 42 and 42' and detent hooks 41 in FIG. 10. In contrast thereto, the detent tongues 55 are arranged outside the membrane 7 however.

This has the advantage inter alia that correct latching of the penetration element 6 on the head piece 5 can also be monitored externally, or, for example should engagement not be achieved correctly, the engagement can be produced manually.

The penetration element 6 is preferably injection-molded with the membrane and the other elements illustrated in FIGS. 11 to 14 as a one-piece molded part made of plastic. Of course multi-part embodiments are also conceivable.

FIGS. 15 to 18 show a head piece 5 provided for the penetration element 6 in FIGS. 11-14 and are described together hereinafter. Here, identical components are provided with reference signs identical to those used in the exemplary embodiments according to the previous figures.

The head piece 5 has a largely circular cylindrical form with a receiving region 60 for arrangement of the container mouth 20 of the container 3. In the receiving region 60, the snap-fit collar 43 is formed on the inner wall and has four inwardly protruding detent protrusions. In the longitudinal direction, the receiving region 60 is defined with respect to a fastening region 62 for the penetration element 6 via an intermediate wall 61 arranged transversely with respect to the longitudinal direction of the head piece 5. The intermediate wall 61 has a central opening 30, which is used for the passage and for the guidance of the hollow needle 9 of the penetration element 6 when said needle is fastened via the membrane 7 to the head piece 5 and is brought into the withdrawal position E.

The intermediate wall 61 additionally has detent recesses 63 for the detent hook pairs 54 of the membrane 7. The recesses 63 are arranged here in an annular manner in an annular receiving indentation 64 for the fastening ring 56 of the membrane 7.

In the fastening region 62, detent recesses 65, which are outwardly open in the radial direction, are formed on the lateral surface and are provided for engagement of the detent tongues 55 of the penetration element 6 when said penetration element is located in the withdrawal position E. Since four detent recesses 65 are provided, the penetration element 6 can be inserted in different orientations into the head piece 5, wherein a latching of the detent tongues 55 in each orientation is ensured.

A receiving region 66 for the filter 11 is formed on the intermediate wall 61 on the side of the receiving space. A circumferential sealing edge 67 of the receiving region 66 is formed in such a way that it rests tightly on the sealing element 4 when the head piece 5 is fitted onto the container 3. The intake openings 23, which connect the fastening region 62 to the receiving region 60, are formed in the intermediate wall 61 in the region of the receiving region 66. If the filter 11 is arranged in the receiving region 66, external air can be aspirated through the intake openings 23 via the filter 11 and fed through the aeration channels 10 of the hollow needle 9 to the interior of the container 3.

Figure 19:
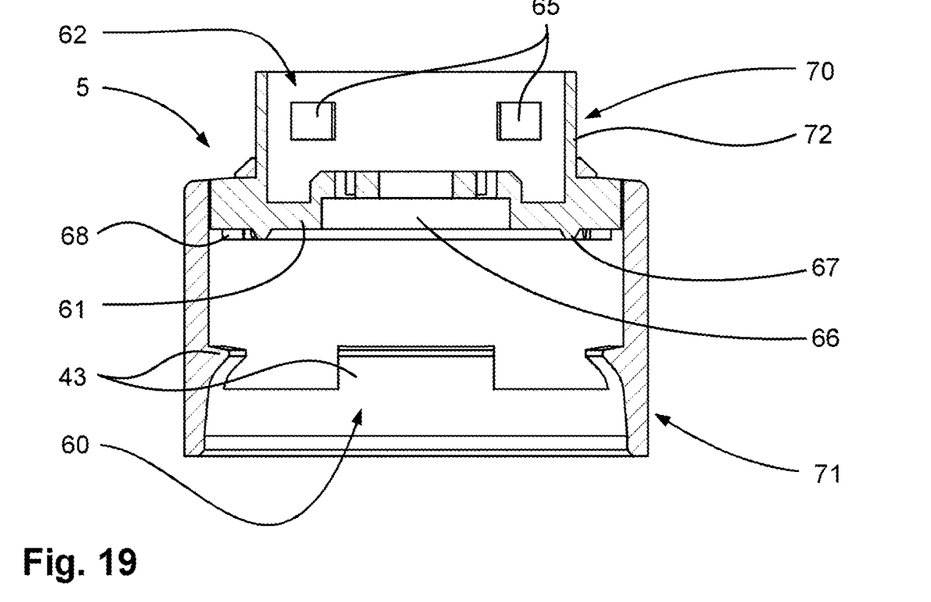
Figure 20:
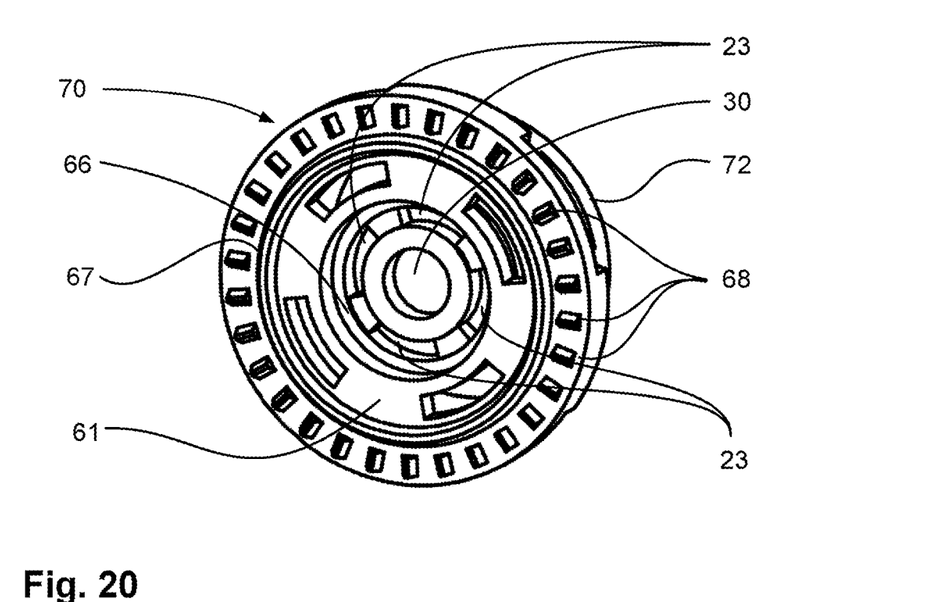
FIG. 20: shows an external oblique view of a coupling part of the head piece according to FIG. 19.

FIGS. 19 and 20 show a further embodiment of the head piece 5 provided for the penetration element 6 in FIGS. 11 to 14 and are described together hereinafter. Here, identical components are provided with reference signs identical to those used in the exemplary embodiments according to the previous figures.

In contrast to the embodiment in FIGS. 15 to 18, the head piece 5 in FIGS. 19 to 20 is formed in two parts, wherein a tubular connection part 71 has a largely circular cylindrical form. An interior of the connection part 71 forms the receiving region 60 for arrangement of the container mouth 20 of the container 3. Similarly to the embodiments in FIGS. 15 to 18, the snap-fit collar 43, which comprises four inwardly protruding detent protrusions, is formed in the receiving region 60 on the inner wall.

The connection part 71 is sealed on one side by a coupling part 70, which comprises the intermediate wall arranged transversely with respect to the longitudinal direction of the head piece 5. The coupling part 70 has a circular cylindrical wall 72, which protrudes outwardly in the longitudinal direction and surrounds the fastening region 62 for the penetration element 6 or the membrane 7.

The coupling part 70 is connected via the intermediate wall 61 to the connection part 71, said intermediate wall sealing the connection part 71 in the manner of a cover. Here, the intermediate wall 61 can be connected in an interlocked or force-locked manner and/or can be integrally bonded to the connection part 71. Similarly to the embodiment in FIGS. 15 to 18, the intermediate wall 61 comprises the detent recesses 63 for the detent hook pairs 54 of the membrane 7 and also the central opening 30, which is used for the passage and for the guidance of the hollow needle 9 of the penetration element 6.

The detent recesses 65, which are provided for engagement of the detent tongues 55 of the penetration element 6, are formed in the embodiment in FIGS. 19 and 20 in the circular cylindrical wall 72 of the coupling part 70. The receiving region 66 for the filter 11 is formed on the intermediate wall 61 on the side of the receiving space. In contrast to the embodiment in FIGS. 15 to 18, the sealing edge 67 is distanced radially outwardly from an edge of the recess 66. The intermediate wall 61 additionally comprises on the side of the receiving space a multiplicity of detent wedges 68, which are arranged radially and prevent a rotation of the container 3 relative to the detent plate 61 due to engagement into the sealing element 4, which for example is resilient. It goes without saying that detent wedges of this type may also be provided in all other embodiments of a head piece.

The head piece in FIGS. 19 and 20 is provided in particular for the attachment to containers having a 20 mm flange.

For all embodiments according to the invention, PET films or polycarbonate films, which are penetrated by the finest of openings, can advantageously be used for example as a filter besides the conventional microfilter membranes. Instead of separately inserted or adhered filters, these could also be integrated directly during injection molding of the respective bearing constructions. A significant advantage of all variants according to the invention also lies in the fact that these can be used for containers having a flange of 13 mm or 20 mm diameter or for containers having flanges of any diameter. In particular, it goes without saying that each embodiment can be adapted accordingly.

The invention claimed is:

1. A device for withdrawing a liquid from a container, which is sealed by a penetrable sealing element, the device comprising a head piece, which is tightly attachable to the sealing element and in which a penetration element is mounted in such a way that the penetration element is displaceable with the aid of guide means between an idle position and a withdrawal position, wherein the penetration element comprises at least one hollow needle, by means of which the sealing element is penetrable in the withdrawal position, with at least one aeration channel for aerating the container as the liquid is withdrawn, wherein the guide means comprise at least one wall portion, which connects the penetration element to the head piece and holds said penetration element in the idle position, wherein the wall portion is deformable in such a way that the wall portion guides the penetration element until the withdrawal position is reached, wherein the wall portion is at least one resilient membrane surrounding the penetration element.

2. The device as claimed in claim 1, wherein the aeration channel is formed as a groove on an outer face of the hollow needle.

3. The device as claimed in claim 1, wherein the device comprises at least one filter, via which air from the atmosphere can be fed in the withdrawal position into the container via the aeration channel.

4. The device as claimed in claim 3, wherein the filter is arranged on the penetration element.

5. The device as claimed in claim 3, wherein the filter is arranged on the head piece.

6. The device as claimed in claim 1, wherein the guide means are connected integrally to the head piece and/or to the penetration element.

7. The device as claimed in claim 1, wherein the guide means comprise fastening means, which, in order to connect the guide means to the head piece, is latchable to the head piece.

8. The device as claimed in claim 1, wherein the head piece is formed in two or more parts, wherein a first part is provided to be coupled to the container and a second part is connected to the penetration element.

9. The device as claimed in claim 1, wherein the penetration element comprises a coupling part.

10. The device as claimed in claim 1, wherein the penetration element comprises detent means, by means of which the penetration element is latchable in the withdrawal position.

11. The device as claimed in claim 10, wherein the detent means are arranged on the penetration element in such a way that they are externally accessible for manipulation by a user.

12. The device as claimed in claim 10, wherein the head piece comprises detent means, which are complementary to the detent means of the penetration element such that the penetration element is latchable by means of its detent means to the head piece.

13. The device as claimed in claim 1, wherein the head piece carries a centering ring for centering the hollow needle.

14. The device as claimed in claim 1, wherein the penetration element is covered in the idle position by a releasable protective cap.

15. The device as claimed in claim 1, wherein, for multiple withdrawals of liquid in the withdrawal position, a valve for sealing the hollow needle, is arranged on the penetration element.

16. The device as claimed in claim 4, wherein the filter is arranged at an atmosphere-side end of the aeration channel.

17. The device as claimed in claim 16, wherein a collar surrounding the hollow needle is arranged at the atmosphere-side end of the aeration channel, and in that the filter is held on the collar.

18. An arrangement comprising a container containing a liquid, a container mouth of said container being sealed by a penetrable sealing element, and also comprising a device as claimed in claim 1, wherein the head piece rests tightly on the sealing element.

* * * * *